United States Patent
Kaneko et al.

(10) Patent No.: US 9,956,031 B2
(45) Date of Patent: May 1, 2018

(54) TREATMENT DEVICE FOR ENDOSCOPE

(71) Applicants: OLYMPUS CORPORATION, Tokyo (JP); Takashi Toyonaga, Hyogo (JP)

(72) Inventors: Tatsuya Kaneko, Tokyo (JP); Takashi Toyonaga, Kobe (JP)

(73) Assignee: OLYMPUS CORPORATION, Tokyo (JP)

( * ) Notice: Subject to any disclaimer, the term of this patent is extended or adjusted under 35 U.S.C. 154(b) by 553 days.

(21) Appl. No.: 14/549,017

(22) Filed: Nov. 20, 2014

(65) Prior Publication Data
US 2015/0148803 A1 May 28, 2015

Related U.S. Application Data

(63) Continuation of application No. PCT/JP2013/080523, filed on Nov. 12, 2013.
(Continued)

(51) Int. Cl.
*A61B 18/12* (2006.01)
*A61B 18/14* (2006.01)
(Continued)

(52) U.S. Cl.
CPC .......... *A61B 18/1447* (2013.01); *A61B 10/04* (2013.01); *A61B 10/06* (2013.01);
(Continued)

(58) Field of Classification Search
CPC ..... A61B 10/04; A61B 10/06; A61B 18/1442; A61B 18/1445; A61B 18/1447;
(Continued)

(56) References Cited

U.S. PATENT DOCUMENTS 5,275,615 A * 1/1994 Rose ...................... A61B 17/29
606/207
5,482,054 A * 1/1996 Slater ................... A61M 1/0043
600/564
(Continued)

FOREIGN PATENT DOCUMENTS

JP H10-506035 A 6/1998
JP 2000-070280 A 3/2000
(Continued)

OTHER PUBLICATIONS

Extended Supplementary European Search Report dated Jun. 17, 2016 in related European Application No. 13 85 5365.6.
(Continued)

*Primary Examiner* — Daniel Fowler
(74) *Attorney, Agent, or Firm* — Scully, Scott, Murphy & Presser, P.C.

(57) ABSTRACT

A treatment device for an endoscope includes a pair of forceps pieces which has forceps surfaces in contact with a subject tissue and are opened and closed with the forceps surfaces facing each other. Concave portions are formed in the central portions of the forceps surfaces to form the forceps surfaces around the concave portions, and on the forceps surfaces, a first region on the proximal end side of the forceps pieces has a plurality of first teeth with top surfaces formed to be unsharp, and a second region on the distal end side of the forceps pieces to the first region has a plurality of second teeth with top surfaces formed to be sharp.

3 Claims, 3 Drawing Sheets

Related U.S. Application Data

(60) Provisional application No. 61/725,645, filed on Nov. 13, 2012.

(51) Int. Cl.
*A61B 10/06* (2006.01)
*A61B 10/04* (2006.01)
*A61B 17/32* (2006.01)
*A61B 18/00* (2006.01)

(52) U.S. Cl.
CPC ...... *A61B 18/1445* (2013.01); *A61B 18/1482* (2013.01); *A61B 18/1492* (2013.01); *A61B 2017/320064* (2013.01); *A61B 2018/00595* (2013.01)

(58) Field of Classification Search
CPC ...... A61B 2018/145; A61B 2018/1452; A61B 2018/1457; A61B 2018/00595; A61B 2017/320064
See application file for complete search history.

(56) References Cited

U.S. PATENT DOCUMENTS

| | | | |
|---|---|---|---|
| 5,613,499 A | | 3/1997 | Palmer et al. |
| 5,797,958 A | * | 8/1998 | Yoon .................... A61B 17/122 606/139 |
| 5,819,738 A | * | 10/1998 | Slater .................... A61B 10/06 600/564 |
| 6,273,887 B1 | | 8/2001 | Yamauchi et al. |
| 6,689,122 B2 | * | 2/2004 | Yamamoto ............. A61B 10/06 606/1 |
| 2003/0144693 A1 | | 7/2003 | Flipo |
| 2004/0087943 A1 | * | 5/2004 | Dycus ................ A61B 17/2909 606/51 |
| 2005/0101952 A1 | | 5/2005 | Lands et al. |
| 2006/0009711 A1 | | 1/2006 | Gingrich et al. |
| 2006/0184198 A1 | * | 8/2006 | Bales .................... A61B 10/06 606/205 |
| 2011/0251608 A1 | * | 10/2011 | Timm .................. A61B 17/295 606/41 |
| 2012/0101501 A1 | | 4/2012 | Nishimura et al. |

FOREIGN PATENT DOCUMENTS

| | | |
|---|---|---|
| JP | 2002-065598 A | 3/2002 |
| JP | 2004-229976 A | 8/2004 |
| JP | 2005-058344 A | 3/2005 |
| JP | 2008-536530 A | 9/2008 |
| JP | 2009-297503 A | 12/2009 |
| WO | 94/17741 A1 | 8/1994 |
| WO | 9609004 A1 | 3/1996 |
| WO | WO 2006/083728 A2 | 8/2006 |

OTHER PUBLICATIONS

Japanese Office Action dated Sep. 9, 2014 from related Japanese Application No. 2014-532171, together with an English language translation.

International Search Report dated Dec. 17, 2013 issued in PCT/JP2013/080523.

* cited by examiner

TREATMENT DEVICE FOR ENDOSCOPE

The present application is a continuation of PCT International Application No. PCT/JP2013/080523, filed on Nov. 12, 2013, which claims priority from provisional U.S. Patent Application No. 61/725,645, filed on Nov. 13, 2012, the content of each of which is incorporated by reference herein.

TECHNICAL FIELD

The present invention relates to a treatment device for an endoscope, and in particular, to a treatment device for an endoscope which is used to apply a high-frequency current.

BACKGROUND ART

In the related art, as one of treatment devices for endoscopes, a treatment device for an endoscope which applies a high-frequency current to a tissue held by a pair of forceps pieces to cauterize and coagulate the tissue and thus performs hemostasis is known. This treatment device for an endoscope is called a high-frequency forceps or the like.

Patent Document 1 describes a hemostatic forceps which is used to apply a high-frequency current. In a pair of forceps pieces, concave portions are provided in the central portions of the opposing forceps surfaces, and the forceps surfaces which are in contact with a tissue are formed in a strip shape having a given width around the concave portions. With this configuration, even if a tissue is held by any portions of the forceps surfaces, the forceps surfaces which are in contact with the tissue have a uniform width, and as a result, cauterization is able to be performed constantly with a uniform width.

CITATION LIST

Patent Documents

Patent Document 1: Japanese Patent Application Laid-Open No. 2005-58344

SUMMARY OF THE INVENTION

Problems to be Solved by the Invention

However, while the high-frequency forceps described in Patent Document 1 have an advantage that cauterization is able to be performed constantly with a uniform width, since the top surfaces of all teeth are formed to be unsharp and thick, there is a problem in that a comparatively large reaction force is applied to the subject tissue sandwiched between the forceps pieces, and the sandwiched tissue slips off from between the forceps pieces.

The invention has been accomplished in consideration of this problem, and an object of the invention is to provide a treatment device for an endoscope capable of reliably holding a subject tissue.

Means for Solving the Problems

In order to solve the above-described problem, the invention suggests the following means.

A treatment device for an endoscope according to a first aspect of the invention includes a pair of forceps pieces which has forceps surfaces in contact with a subject tissue and are opened and closed with the forceps surfaces facing each other, in which concave portions are formed in the central portions of the forceps surfaces to form the forceps surfaces around the concave portions, and on the forceps surfaces, a first region on the proximal end side of the forceps pieces has a plurality of first teeth with top surfaces formed to be unsharp, and a second region on the distal end side of the forceps pieces to the first region has a plurality of second teeth with top surfaces formed to be sharp.

According to a second aspect of the invention, in the treatment device for an endoscope of the first aspect, the thickness of the second teeth may be thinner than the thickness of the first teeth when viewed from the forceps surface side.

According to a third aspect of the invention, in the treatment device for an endoscope of the first aspect, in a state where the pair of forceps pieces are closed, the forceps surfaces in the first region may be separated from each other at a predetermined distance to be not in contact with each other.

Advantageous Effect of the Invention

In the treatment device for an endoscope of each aspect, since the top surfaces of the teeth of the second region are formed to be sharp and are meshed in a state where a pair of forceps pieces is closed, a large pressure is applied to the sandwiched subject tissue by ridgelines, and the subject tissue rarely slips from the teeth. Therefore, it is possible to reliably hold the subject tissue.

MODE FOR CARRYING OUT THE INVENTION

Hereinafter, an embodiment of the invention will be described referring to FIGS. 1 to 6.

Figure 1:
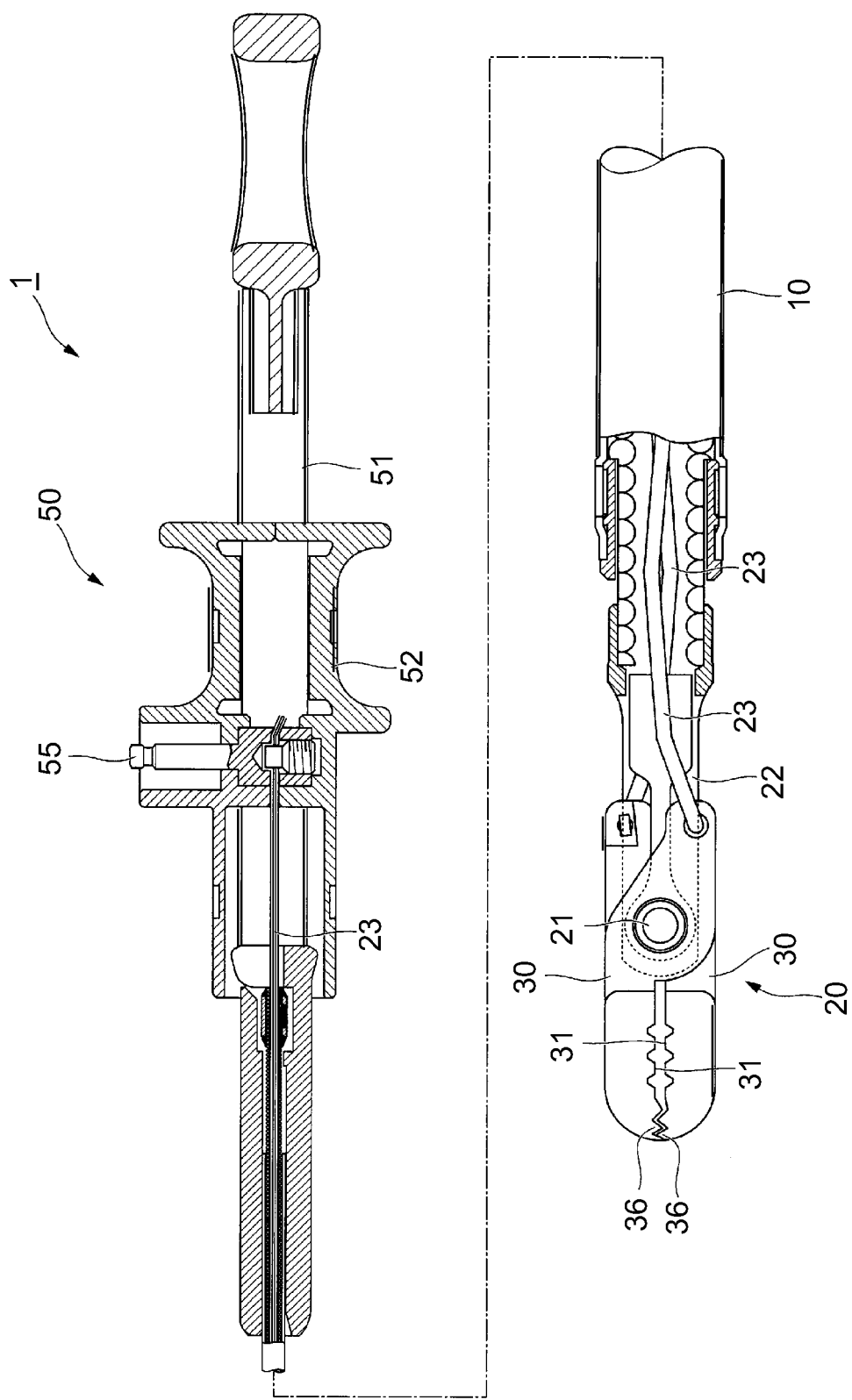
FIG. 1 is a view illustrating the overall configuration of a treatment device for an endoscope according to an embodiment of the invention.

FIG. 1 is a view illustrating the overall configuration of a high-frequency forceps 1 which is a treatment device for an endoscope of this embodiment. The high-frequency forceps 1 includes a flexible elongated insertion part 10, a treatment part 20 which is attached to the distal end portion of the insertion part 10, and an operating part 50 which is attached to the proximal end portion of the insertion part 10.

The insertion part 10 is formed of resin, coil, and the like in a tubular shape having a lumen, and operating wires described below are retractably inserted thereinto.

The treatment part 20 is constituted by connecting a pair of forceps pieces 30 to relatively rotate around a rotating shaft 21. Since the rotating shaft 21 is fixed to a base 22 fixed to the distal end of the insertion part 10, the rotating shaft 21 is fixed with respect to the insertion part 10. Operating wires 23 are connected to the proximal end portions of a pair of forceps pieces 30. Each operating wire 23 is connected to the operating part 50 through the lumen of the insertion part 10.

The operating part 50 includes an operating part body 51 which is fixed to the proximal end portion of the insertion part, and a slider 52 which is slidably attached to the operating part body 51 in the longitudinal direction, and the basic configuration thereof is known. The proximal end portion of each operating wire 23 extending through the inside of the insertion part 10 protrudes into the internal space of the operating part body 51 and is fixed to the slider 52. Accordingly, the slider 52 slides with respect to the operating part body 51, whereby the two operating wires 23 are able to be advanced and retracted with respect to the insertion part 10. As described above, since the rotating shaft 21 is fixed to the insertion part 10, the respective forceps pieces 30 rotate around the rotating shaft 21 with the advancement and retraction of the operating wires 23, and a pair of forceps pieces 30 is opened and closed.

The slider 52 is provided with a plug 55 which is connected to an external high-frequency power supply. Since the plug 55 is electrically connected to the respective operating wires 23, a high-frequency current is able to be applied from the plug 55 to the pair of forceps pieces 30 through the operating wires 23.

Figure 2:
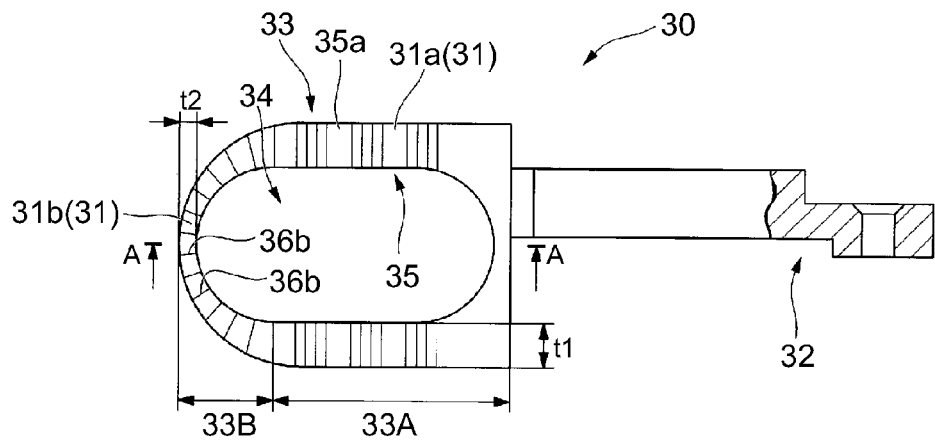
FIG. 2 is a view when a forceps piece constituting a treatment part is viewed from a forceps surface side.
Figure 3:
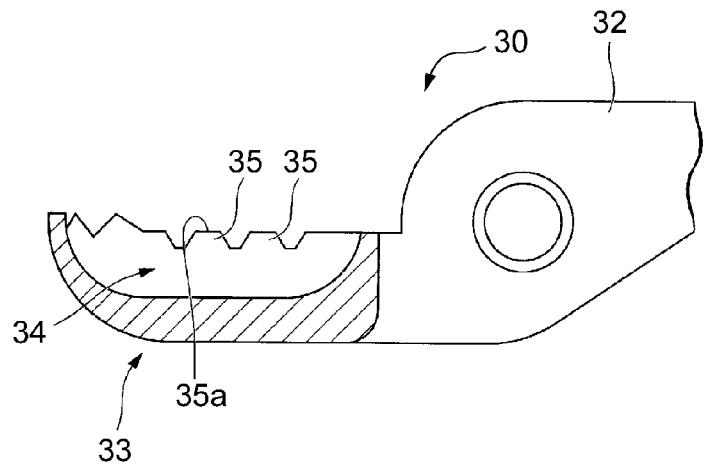
FIG. 3 is a sectional view taken along the line A-A of FIG. 2.

The opposing surfaces in the rotation direction of the pair of forceps pieces 30 are forceps surfaces 31 which are in contact with a tissue. FIG. 2 is a view when the forceps piece 30 is viewed from the forceps surface 31 side, and FIG. 3 is a sectional view taken along the line A-A of FIG. 2. The forceps piece 30 has a base part 32 which is connected to the rotating shaft, and a holding part 33 which is provided on the distal end side of the base part 32, and the forceps surface 31 is provided in the holding part 33.

A bottomed concave portion 34 having a predetermined depth is provided in the central portion of the forceps surface 31. With this, the forceps piece 30 is formed in a substantially cup shape which opens to the forceps surface 31 side, and the forceps surface 31 is formed at a predetermined width around the concave portion 34.

In a state where the forceps piece 30 is viewed in the direction normal to the forceps surface 31, the concave portion 34 is formed in an elliptical shape. The holding part 33 is also formed in a substantially elliptical shape excluding the proximal end side. With this, the holding part 33 is provided with a proximal end-side first region 33A and a distal end-side second region 33B.

In a forceps surface 31a of the first region 33A, unevenness is provided at a predetermined interval in a radial direction to provide a plurality of teeth (first teeth) 35. The first region 33A constitutes a substantially rectangular intermediate portion of the substantially elliptical holding part 33, a region of the elliptical concave portion 34 in the first region 33A has a substantially rectangular shape, the forceps surface 31a of the first region 33A is formed in a substantially linear shape with a substantially uniform width, and the thickness of the teeth 35 provided in the forceps surface 31a (the dimension in a direction orthogonal to the radial direction, in which the forceps surface 31 extends, on the forceps surface 31) is substantially constant. In this embodiment, the thickness t1 of the teeth 35 is, for example, equal to or greater than 0.25 millimeters (mm) and equal to or less than 0.4 mm, and the top surface 35a of each of the teeth 35 is flat, and is formed to be unsharp with no clear ridgelines. That is, a plurality of teeth 35 has no sharp portions.

Figure 4:
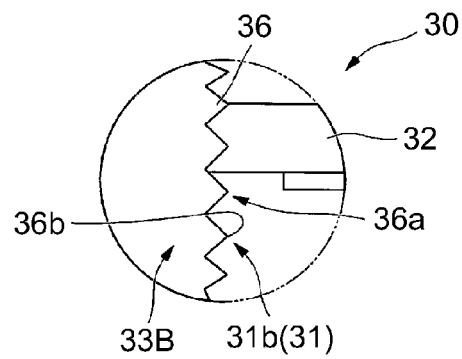
FIG. 4 is a view when the forceps piece is viewed from a distal end side.

FIG. 4 is a view when the forceps piece 30 is viewed from the distal end side. In a forceps surface 31b of the substantially semicircular second region 33B, a plurality of teeth (second teeth) 36 arranged in the radial direction is also formed. As illustrated in FIG. 2, in the second region 33B, the farther from the first region 33A, the thinner the thickness of the forceps surface 31b and the teeth 36 is. That is, the thickness t2 of the teeth on the distal end side is thinner than the proximal end side when viewed from the forceps surface 36b. The minimum value t2 of the thickness of the teeth 36 near the distal end of the second region 33B is equal to or greater than 0.15 mm and equal to or less than 0.25 mm. Each of the teeth 36 formed in the second region 33B is formed with the top surface 36a to be sharp having a ridgeline (forceps surface) 36b, unlike the teeth 35 of the second region 33B. That is, a plurality of teeth 36 has sharp portions.

It is preferable that the thickness t2 of the teeth 36 when viewed from the forceps surface 36b side is thinner than the thickness t1 of the teeth 35.

As illustrated in FIG. 1, the upper and lower teeth 36 of the second region 33B are configured to mesh with each other in a state where a pair of forceps pieces 30 is closed. In the first region 33A, in a state where a pair of forceps pieces 30 is closed, the forceps surfaces 31 face each other at a predetermined distance such that the top surfaces 35a of the upper and lower teeth 35 are not in contact with each other. In this embodiment, the forceps surface means a surface including the uppermost side of a plurality of teeth. That is, the forceps surface of the first region 33A is flush with the top surfaces 35a of the teeth 35, and forceps surface of the second region 33B is flush with the ridgelines 36b of the teeth 36.

The operation of the treatment device 1 for an endoscope of this embodiment configured as above at the time of the use will be described.

A user first introduces an endoscope (not shown) into the body of a patient and moves the distal end portion of the endoscope near the subject tissue to be processed. Next, the treatment device 1 for an endoscope is inserted into a forceps channel of the endoscope from the treatment part 20 side, and the treatment part 20 protrudes from the distal end opening of the forceps channel.

Figure 5:
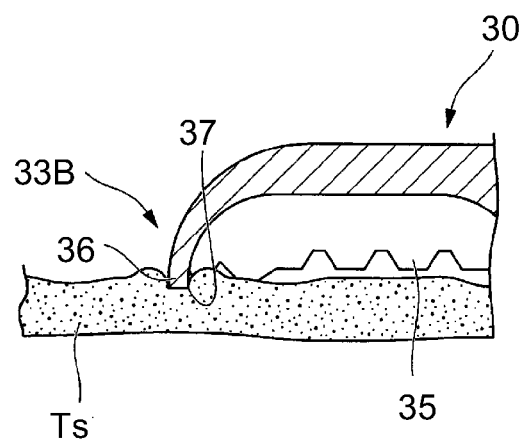
FIG. 5 is a view illustrating a process at the time of the use of the treatment device for an endoscope.

The user operates the slider 52 of the operating part 50 while confirming the subject tissue in the visual field of the endoscope to open a pair of forceps pieces 30, and closes the forceps pieces 30 in a state where part of the subject tissue is placed between the forceps pieces 30 to hold the subject tissue. At this time, as illustrated in FIG. 5, the teeth 36 formed in the distal end-side second region 33B first bite into the subject tissue Ts, and the subject tissue Ts is sandwiched between a pair of forceps pieces 30 while being engaged with a proximal end-side edge 37 of the teeth 36.

When holding the subject tissue Ts, the subject tissue Ts sandwiched between the teeth 36 of the second region 33B is compressed in a direction orthogonal to the forceps surface 31, whereby a reaction force to return to the original shape is generated. The reaction force increases in proportion to the area of the subject tissue Ts to be compressed.

In the treatment device 1 for an endoscope of this embodiment, since the top surfaces 36a of the teeth 36 of the second region 33B are formed to be sharp and meshed with each other in a state where a pair of forceps pieces 30 is closed, a large pressure is applied to the sandwiched subject tissue by the ridgelines 36b, and the subject tissue Ts rarely slips from the teeth 36.

The thickness of the teeth 36 is set to be thinner than the teeth 35 of the first region 33A, and the contact area of the teeth 36 to the subject tissue is smaller than the contact area of the teeth 35. For this reason, the teeth 36 bite into the subject tissue Ts with a force smaller than the teeth 35, and the subject tissue Ts is reliably held between the forceps pieces.

When the subject tissue Ts is sandwiched between a pair of forceps pieces 30, the thickness of the forceps surface 31 in contact with the subject tissue Ts is set to be thinner in the second region 33B in contact with the subject tissue Ts earlier. As a result, the reaction force is rarely applied to the subject tissue sandwiched between the forceps pieces to move off from the forceps, and the subject tissue is able to be reliably held between the forceps pieces.

Figure 6:
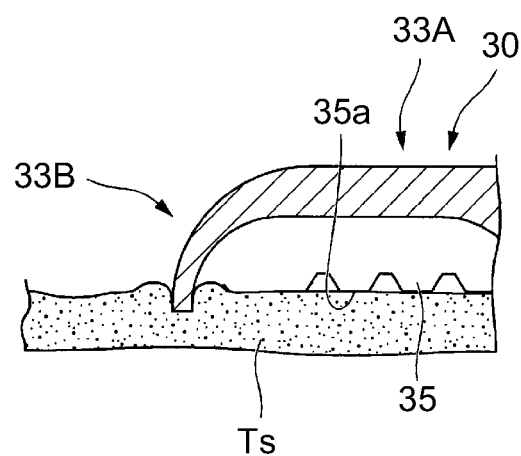
FIG. 6 is a view illustrating a process at the time of the use of the treatment device for an endoscope.

If the user further closes a pair of forceps pieces 30, the subject tissue Ts is further sandwiched between the forceps pieces 30, as illustrated in FIG. 6, the upper and lower teeth 35 of the first region 33A are brought into contact with the subject tissue Ts. In this state, if the user supplies the high-frequency current to the plug 55, the high-frequency current is supplied between a pair of forceps pieces 30 through the operating wires 23, and the subject tissue Ts sandwiched between the forceps pieces 30 is cauterized. At this time, in a state where the teeth 35 of the first region 33A with the top surfaces 35a formed to be unsharp are in contact with the subject tissue reliably held between a pair of forceps pieces 30, the high-frequency current is applied to the treatment part 20. Accordingly, contact with the subject tissue is made through a large area and the high-frequency current is applied, whereby a large area is able to be cauterized and coagulated to reliably perform a desired operation, such as hemostasis.

In this way, in the treatment device 1 for an endoscope of this embodiment, it becomes possible to perform an operation while achieving two matters of reliably holding the subject tissue between the forceps pieces and cauterizing and coagulating a large area at the time of the application of the high-frequency current at high level.

Although the embodiment of the invention has been described, the technical scope of the invention is not limited to the foregoing embodiment, and the combination of components may be changed or the respective components may be altered in various ways or deleted without departing from the spirit and scope of the invention.

For example, in the treatment device for an endoscope of the invention, the ratio of the first region and the second region, and the specific shapes and the dimension of the first region and the second region, and the like are not particularly limited, and may be appropriately set. For example, the second region may have a shape of protruding toward the distal end side, not a semicircular shape.

In a state where a pair of forceps pieces is closed, the distance between the forceps surfaces in the first region may not be the same over the first region. For example, the distance between the forceps surfaces may be set to gradually increase toward the proximal end side. In this case, the distance between the forceps surfaces gradually increases toward the proximal end side, whereby the volume of the subject tissue received between the forceps pieces in the first region increases when the forceps is closed toward the proximal end side. For this reason, there is no case where an excessive force is applied to the subject tissue held in the first region to cause damage to a tissue, and it is possible to bring the subject tissue into contact with the top surfaces of the first teeth.

INDUSTRIAL APPLICABILITY

In the treatment device for an endoscope of the foregoing embodiment, since the top surfaces of the teeth of the second region are formed to be sharp and meshed with each other in a state where a pair of forceps pieces is closed, a large pressure is applied to the sandwiched subject tissue by the ridgelines, and the subject tissue rarely slips from the teeth. Accordingly, it is possible to reliably hold the subject tissue.

DESCRIPTION OF REFERENCE NUMERALS

1: high-frequency forceps (treatment device for an endoscope)
30: a pair of forceps pieces
31: forceps surface
33A: first region
33B: second region
34: concave portion
35: teeth (first teeth)
36: teeth (second teeth)

The invention claimed is:
1. A treatment device comprising:
a treatment part sized to be inserted through a channel of an endoscope and protruded from a distal end of the channel of the endoscope, wherein the treatment part comprises:
a rotating shaft;
a first forceps piece extending along an extension axis, wherein the first forceps piece comprises:
a first base part rotatably connected to the rotating shaft; and
a first holding part; and
a second forceps piece extending along the extension axis, wherein the second forceps piece comprises:
a second base part rotatably connected to the rotating shaft; and
a second holding part,
wherein the first base part and the second base part are configured to rotate the first holding part relative to the second holding part about the rotating shaft between a fully closed position and a fully open position to change a distance between the first holding part and the second holding part,
wherein each of the first holding part and the second holding part comprises an inner circumferential wall and an outer circumferential wall between which a plurality of teeth are defined,
wherein for the each of the first holding part and the second holding part:
a first group of teeth of the plurality of teeth is provided in a distal region along the extension axis, and a second group of teeth of the plurality of teeth is provided in a proximal region that is proximal to the distal region along the extension axis;
a first thickness of the first group of teeth is defined as a distance between the inner circumferential wall and the outer circumferential wall in the distal region, and a second thickness of the second group of teeth is defined as a distance between the inner circumferential wall and the outer circumferential wall in the proximal region;
a smallest value of the second thickness is greater than a largest value of the first thickness;
a tooth in the first group of teeth that is furthest from the second group of teeth along the extension axis has a smallest value of the first thickness;
a tooth in the first group of teeth tapers, in an extending direction away from the extension axis, to form a ridgeline;

a tooth in the second group of teeth tapers in the extending direction away from the extension axis, to a top surface that is less sharp than the ridgeline;

the ridgeline of the tooth in the first group of teeth extends further in the extending direction than the top surface of the tooth in the second group of teeth, wherein in the fully closed position:

the first group of teeth of the first holding part and the first group of teeth of the second holding part are configured to contact each other;

the top surface of the tooth in the second group of teeth of the first holding part faces the top surface of the tooth in the second group of teeth of the second holding part in the extending direction; and the top surface of the tooth in the second group of teeth of the first holding part is separated from the top surface of the tooth in the second group of teeth of the second holding part by a predetermined distance in the extending direction, and wherein at least the second group of teeth of each of the first forceps piece and the second forceps piece are electrically connected to a high-frequency power supply to apply a high-frequency current to a target object held between the first forceps piece and the second forceps piece.

2. The treatment device according to claim 1, wherein the first thickness is measured in a direction orthogonal to the inner circumferential wall in the distal region, and wherein the second thickness is measured in a direction orthogonal to the inner circumferential wall in the proximal region.

3. The treatment device according to claim 1, further comprising:

an operating part;

a tubular insertion part;

a base configured to be fixed to a distal end of the tubular insertion part, wherein the rotating shaft is configured to be fixed to the base such that the rotating shaft is fixed with respect to the tubular insertion part; and one or more operating wires configured to connect at least one of the first forceps piece and the second forceps piece to the operating part, wherein the one or more operating wires are moved by the operating part to thereby rotate the first holding part relative to the second holding part about the rotating shaft between the fully closed position and the fully open position.

* * * * *